(12) United States Patent
Hirabayashi et al.

(10) Patent No.: US 6,787,017 B1
(45) Date of Patent: Sep. 7, 2004

(54) CAPILLARY ELECTROPHORETIS SYSTEM, SAMPLE ANALYZER AND LIQUID SAMPLE CASSETTE FOR ELECTROPHORETIC SEPARATION

(75) Inventors: Atsumu Hirabayashi, Kodaira (JP); Yukiko Hirabayashi, Kokubunji (JP); Akihiko Okumura, Hachioji (JP); Hideaki Koizumi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/806,913
(22) PCT Filed: Oct. 9, 1998
(86) PCT No.: PCT/JP98/04560
§ 371 (c)(1), (2), (4) Date: Apr. 6, 2001
(87) PCT Pub. No.: WO00/22426
PCT Pub. Date: Apr. 20, 2000

(51) Int. Cl.[7] .............................................. G01N 27/447
(52) U.S. Cl. .................... 204/603; 204/601; 204/602
(58) Field of Search ................................ 204/601, 603, 204/602, 612; 422/70

(56) References Cited

U.S. PATENT DOCUMENTS

| 5,630,924 A | * | 5/1997 | Fuchs et al. ................. 204/601 |
| 6,017,434 A | * | 1/2000 | Simpson et al. ............. 204/612 |
| 6,110,343 A | * | 8/2000 | Ramsey et al. ............. 204/601 |
| 6,413,782 B1 | * | 7/2002 | Parce et al. ................. 436/514 |

FOREIGN PATENT DOCUMENTS

| JP | 5-93711 | 4/1993 |
| JP | 5-507793 | 11/1993 |
| JP | 8-233778 | 9/1996 |
| JP | 8-304339 | 11/1996 |
| JP | 8-334505 | 12/1996 |

OTHER PUBLICATIONS

Trends in Analytical Chemistry, vol. 16, No. 1, 1997, pp. 45–52.

Analytical Chemistry, vol. 65, No. 19, Oct. 1, 1993, pp. 2637–2642.

Analytical Chemistry, vol. 69, No. 3, Feb. 1, 1997, pp. 426–430.

* cited by examiner

*Primary Examiner*—Nam Nguyen
*Assistant Examiner*—Brian L Mutschler
(74) *Attorney, Agent, or Firm*—Mattingly, Stanger & Malur, P.C.

(57) ABSTRACT

The capillary electrophoresis system includes a wafer-shaped part having passages filled with a buffer solution for introducing sample solutions; a body having a configuration suitable to removably hold and to move the wafer-shaped part. The body includes first and second electrodes for applying a voltage across both ends of passages of the wafer-shaped part to separate and remove the sample solution. The body also includes first and second buffer reservoirs conductive to passages of the wafer-shaped part at specific positions for filling buffer solution around the first and second electrodes. The system according to the present invention facilitates washing of electrophoresis passages and reduces the time and labor costs required for replacement of the fused-silica wafers and simplifies operation by allowing a plurality of sample solutions to be analyzed more quickly.

12 Claims, 8 Drawing Sheets

CAPILLARY ELECTROPHORETIS SYSTEM, SAMPLE ANALYZER AND LIQUID SAMPLE CASSETTE FOR ELECTROPHORETIC SEPARATION

BACKGROUND OF THE INVENTION

1. Field of the Invention

The present invention relates to a capillary electrophoresis system, sample analyzing system and sample cassette, and more particularly to a capillary electrophoresis system suitable to be connected to a sample analyzing system such as a mass spectrometer.

2. Description of the Prior Art

A capillary electrophoresis system having fine passages defined in a fused-silica wafer is well known in the art as described in "Analytical Chemistry", vol. 65, pp. 2637–2642 (1993).

Passages cited in this paper are constituted of an inlet passage for introducing liquid sample and a passage for electrophoresis that is perpendicularly defined to the inlet passage. The size of cross-section of these passages may be approximately 12 micrometers in depth, 50 micrometers in width, and 30 millimeters in length.

At the ends of passages, electrodes are provided. All of the passages are filled with buffer solution first and liquid sample is injected at one end of the sample inlet passage. Thereafter the liquid sample is introduced into the passage by applying a voltage at the level of approximately few kilovolts between the electrodes placed at the both ends of sample inlet passages, whereby the introduction of liquid sample into the passage for electrophoresis completes. By applying a voltage of approximately few kilovolts to the electrodes placed at the both ends of the passages for electrophoresis the liquid sample introduced to the passage is separated by the electrophoresis phenomenon. The time required for the separation is approximately 10 seconds.

SUMMARY OF THE INVENTION

The capillary electrophoresis system of the Prior Art as have been described above has an advantage that it can separate one sample in a relatively short time. However, such a system needs to perform a cleaning procedure of the electrophoresis passages or to replace the fused-silica wafer with a new one. As a result, in order to perform a series of specimens sequentially, a considerable labor and time are required.

In addition, the capillary electrophoresis system of the Prior Art as have been described above may need to introduce the liquid sample directly onto the wafer. Since the sample inlet on the wafer is very fine and there are electrodes to which a high voltage is applied, the introduction of sample requires the operator to perform a complex work.

The present invention has been made in view of the above circumstances and has an object to overcome the above problems.

An object of the present invention is to provide a capillary electrophoresis system and a sample analyzing system capable of analyzing a plurality of samples in a relatively short time.

Another object of the present invention is to provide a capillary electrophoresis system, which facilitates to clean the passages and has passages for repetitive use.

Still another object of the present invention is to provide a capillary electrophoresis system and a sample cassette for electrophoresis capable to carry a sample loaded therein.

To achieve the objects and in accordance with the purpose of the invention, as embodied and broadly described herein, this invention comprises a capillary electrophoresis system, having a wafery part having passages to flow liquid sample; and a body having a configuration so as to move the wafery part to setting in a relative manner. The body includes first and second electrodes for applying a voltage across both ends of passages of the wafery part to separate the sample solution and first and second buffer reservoirs conductive to the passages of the wafery part at a specific position for filling buffer solution around the first and second electrodes.

In addition, the present invention provides a capillary electrophoresis system, comprising: a cartridge-typewafery part including a plurality of passages, a body having a buffer reservoir conductive to the passages of wafery part, for maintaining the wafery part in a removable and setting configuration.

In addition, in accordance with the present invention, during analysis, liquid sample will be loaded into the plurality of passages provided on the cartridge-type watery part, then the wafery part is attached to the capillary electrophoresis system, then the liquid sample will be electrophoretically separated by relatively moving the wafery part having the liquid sample loaded with the capillary electrophoresis system to performing a separation of several kinds of materials in the liquid sample into bands.

As a result, separation of each sample, or separation for obtaining an electrophoresis migration time pattern of a single sample may be completed in a shorter time. Consequently a complex operation for introducing samples will be eliminated.

In addition, the present invention provides a liquid sample cassette for use in an electrophoresis separation comprising a wafery part (wafer-shaped part) having passages filled with a solution, attached to a removable holder.

In addition, the present invention provides a sample analyzing system comprising a capillary electrophoresis system and an analyzer. The capillary electrophoresis system includes a wafery part having passages for flowing a solution, a body having a structure for relatively moving the wafery part in setting by maintaining the wafery part in a removable configuration. The body further comprises: first and second electrodes for applying a voltage across the passage in the wafery part to perform an electrophoresis separation to extract the solution through an end; and first and second buffer solution reservoir conductive to the solution in the passages in the wafery part at a specific position for filling buffer solution on and around both the first and second electrodes. The analyzer optically detects the solution having electrophoresis separation performed by the capillary electrophoresis system to analyze.

In addition, the present invention provides a sample analyzing system comprising a capillary electrophores is system, an ion source, and a mass spectrometer. The capillary electrophoresis system includes a wafery part having passages for flowing a liquid solution, and a body having a structure suitable for maintaining the wafery part in a removable configuration and for relatively moving the wafery part in a setting configuration. The body includes first and second electrodes for applying a voltage across both ends of passages of the wafery part to extract a solution from one end by electrophoresis separation, and first and second buffer reservoirs conductive to the solution in the wafery part at a specific position, for filling buffer solution on and around the first and second electrodes. The ion source is connected to one of buffer reservoirs in the capillary electrophoresis system to ionize the solution flowing through the wafery part into gaseous ions. The mass spectrometry performs mass analyses of the ions produced by the ion source.

The above and further objects and novel features of the present invention more fully appear from following detailed description when the same is read in connection with the accompanying drawings. It is to be expressly understood, however, that the drawings are for the purpose of illustration only and not intended as a definition of the limits of the present invention.

DETAILED DESCRIPTION OF THE PREFERRED EMBODIMENTS

A detailed description of one preferred embodiment embodying the present invention is now given referring to the accompanying drawings.

Figure 1:
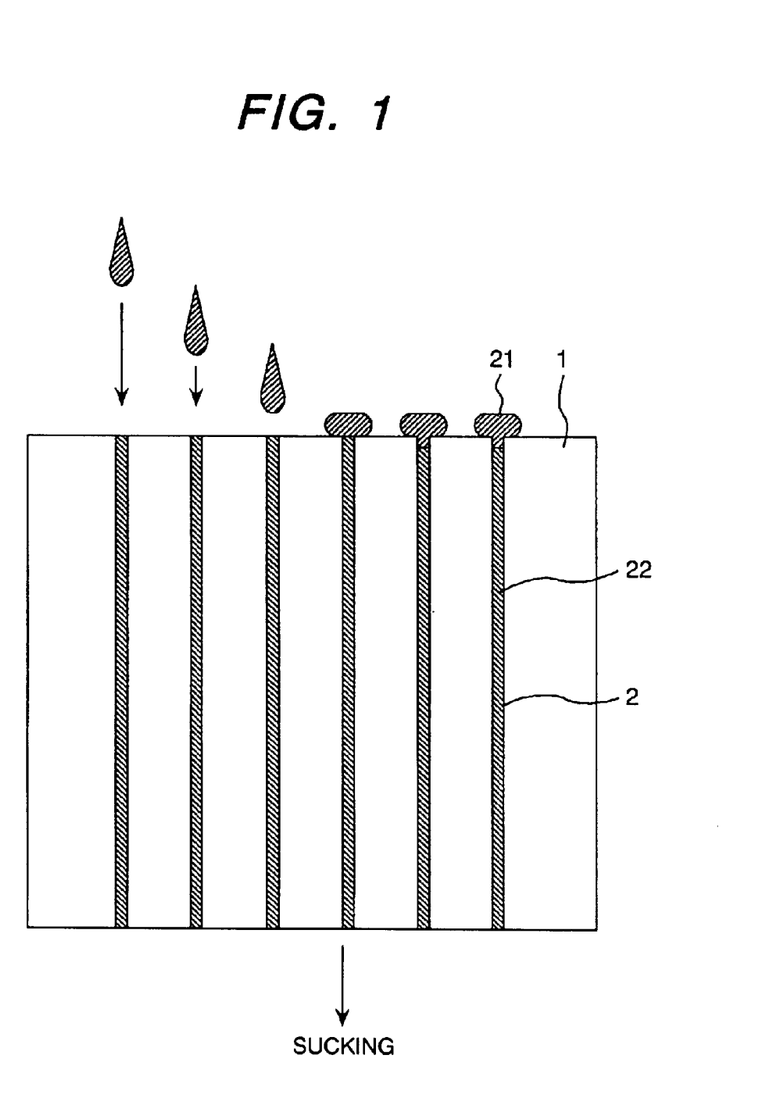
FIG. 1 is a schematic cross-sectional view in a direction of wafery part, illustrating a first embodiment of wafery part in accordance with the present invention.

Now referring to FIG. 1, there is shown a schematic cross-sectional view in the direction of wafery part of first embodiment of a cartridge-type wafery part 1. The cartridge-type wafery part 1 may be formed from a dielectric material such as quartz glass or a resin.

On the wafery part 1 there are provided a plurality of passages 2 each having the same shape in their profile. The sectional area of the passages 2 may be equal to or less than 100 micrometers, and in a typical embodiment the passages 2 may be formed in a rectangle of the size of 10 micrometers by 60 micrometers.

It may be advantageous for producing a wafery part 1 having a plurality of passages 2 as have been described above by bonding a plate having channels with another plate. To process the channels a dry etching technology may be applicable. The wafery part may also be made by embedding a fused-silica capillary having inner diameter of less than 50 micrometers into channels.

As shown in FIG. 1, the passages 2 (or capillaries) are filled with a liquid solution. Because of the fine cross-sectional area of passages 2 the solution is likely to be sucked therein due to the capillarity, so that the solution thereby will fill the passages 2 easily. However, if needed the solution may be loaded by means of a forced suction.

Figure 2A:
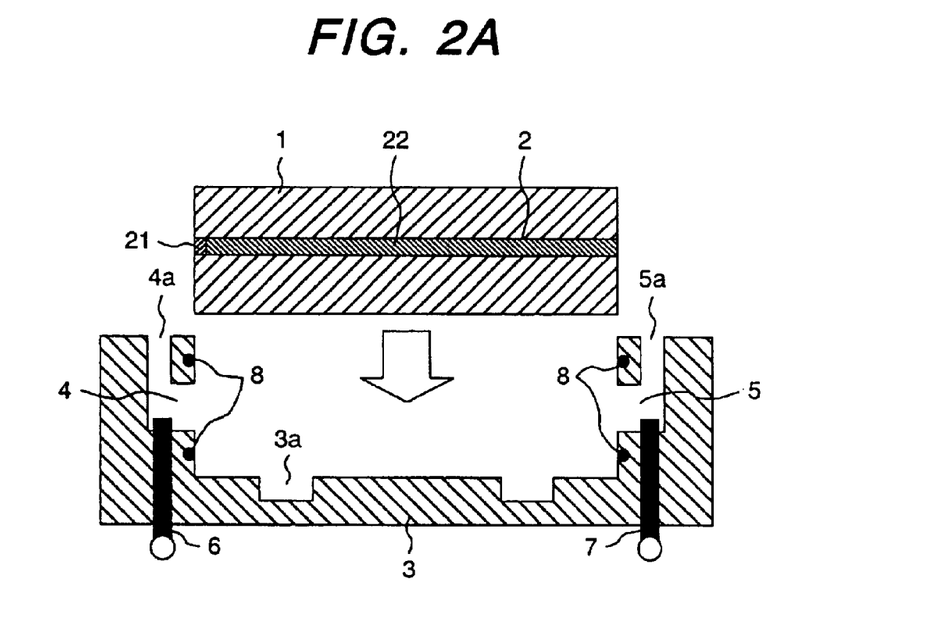
FIG. 2A is a schematic cross-sectional view in the vertical direction before attaching the wafery part of the first embodiment of capillary electrophoresis system of the present invention into the system.
Figure 2B:
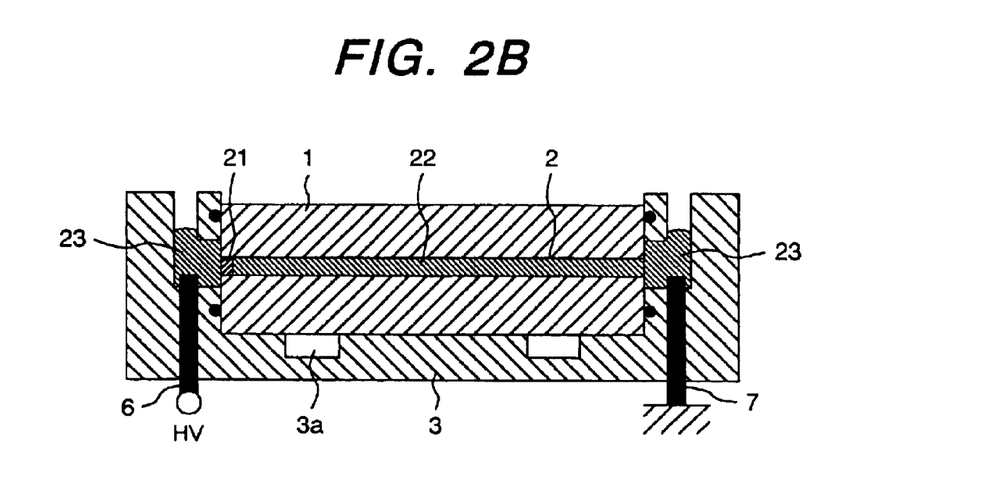
FIG. 2B is a schematic cross-sectional view in the vertical direction illustrating buffer reservoirs fulfilled with buffer solution and wafery part attached to the body in the first embodiment of capillary electrophoresis system in accordance with the present invention.
Figure 3:
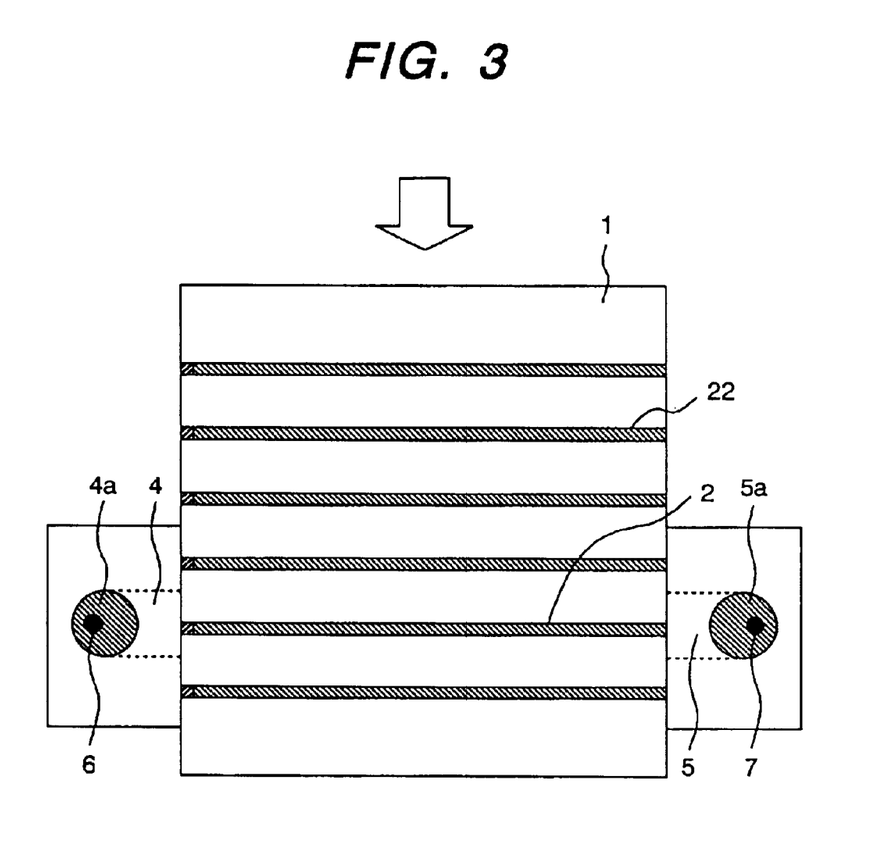
FIG. 3 is a top view of the first embodiment of capillary electrophoresis system in accordance with the present invention.

To perform a capillary electrophoresis system, buffer solution 22 (any desired buffer solution may be used, including PBS) are preloaded into the passages 2 (or capillaries). Then, a liquid sample 21 containing a variety of materials is loaded through one end of the passages 2(or capillaries). In the liquid sample 21, charged particles (ionized particles) and neutralized molecules may be contained in general. Then, as shown in FIG. 2B and FIG. 3, a high voltage is applied across both ends of the passages 2 (capillaries) to effectuate an electrophoresis separation. In order to make a good electrical contact, the electrodes 6 and 7 for applying the voltage are dipped into a conductive solution 23 such as the buffer solution as well as the terminus of capillary.

In FIG. 1, the liquid sample 21 is illustrated as liquid drops falling from the top, and the solution filled in the passages 2 is the buffer solution 22. In FIG. 2, the liquid sample 21 is in the leftmost part of the passages 2 and other part is filled with the buffer solution 22 and 23.

To fill the buffer solution 22 in the passages 2 (in the capillaries) of the watery part 1, the capillarity phenomenon may be used. However, a syringe may also be used for pumping or sucking. Then the liquid sample 21 is to be loaded by making use of gravitational suction or electrophoresis suction.

The volume of the liquid sample 21 may differ depending on the operation technique for suction. For example, in the gravity method the flow rate of the liquid sample sucked may be precalculated, so that the volume of the liquid sample 21 can be determined by controlling the duration of suction time. In cases in accordance with the present invention, the use of gravity method and electrophoresis method has not a significant advantage when compared to the use of other methods. Indeed the suction by using a pump or a syringe may rather be convenient. In such a case the volume of the liquid sample 21 to be sucked can be measured by the syringe used to determine the volume of the sucked liquid sample 21. The cross-sectional area of the passages 2 (or capillaries) is very fine and known, so that the liquid sample 21 contained in the capillary have approximately 1 millimeter in length. The volume of the sucked liquid sample 21 can be determined by measuring the length of either the buffer solution 22 or the liquid sample 21 in condition that the buffer solution 22 can be distinguished from the liquid sample 21.

As can be appreciated from the foregoing description, since the liquid sample 21 can be introduced in an easy way into a plurality of passages 2 (or capillaries) of the wafery part 1, as well as since the wafery part 1 can be detached from the capillary electrophoresis system device in order to rinse the passages 2, the wafery part 1 may be suitable for reuse.

Now referring to FIG. 2, there is shown a schematic cross-sectional view in the vertical direction of the first embodiment of the capillary electrophoresis system in accordance with the present invention. FIG. 2A is a schematic diagram immediately before the wafery part 1 is attached to the device 3, while FIG. 2B is the wafery part 1 attached to the device 3. As shown in FIG. 2A, the wafery part 1 having a fluid containing the liquid sample 21 and the buffer solution 22 introduced into a plurality of passages 2 being attached (mounted) to the device 3 of the capillary electrophoresis system as shown in FIG. 2B. The device 3 is made of a dielectric material such as a fused silica and a resin, as similar to the wafery part 1. On the device 3 there are provided a first buffer reservoir 4 and a second buffer reservoir 5. As shown in FIG. 2B, the conductive solution 23 is poured into the first buffer reservoir 4 and the second buffer reservoir 5 after attaching the wafery part 1 to the device 3 in order to prevent any bubbles from being introduced into the passages 2 of the wafery part 1.

The first buffer reservoir 4 and the second buffer reservoir 5 of the device 3 of capillary electrophoresis system have a first electrode 6 and a second electrode 7, respectively, through which electrodes a voltage will be applied to the conductive buffer solution 23 and ultimately to the liquid sample 21 in the passages 2 (or capillaries) in order to perform an electrophoresis separation.

On or near the first electrode 6 and the second electrode 7 the buffer solution 23 may develop gases, which may form bubbles. When such bubbles may be in the passages 2 the electrophoresis will malfunction. Therefore a path 4a and a path 5a above the first electrode 6 and the second electrode 7 will be provided for respective the first buffer reservoir 4 and the second buffer reservoir 5, both of paths communicating respective reservoirs into the ambient air. The buffer solution 23 contained in the first buffer reservoir 4 and the second buffer reservoir 5 may be in direct contact with the ambient air so that through these paths 4a and 5a it will be capable of releasing bubbles developed in the fluid to the environment.

By monitoring the electrophoresis current the bubbles aberrant into the passages 2 can also be detected.

As shown in FIG. 2B, one ends of both the first electrode 6 and the second electrode 7 are in direct contact with the buffer solution 23. In order to protect the operator from electric shock, the terminus of the first electrode 6 and the second electrode 7 in contact with the buffer solution 23 may be shielded so as to minimize the exposed part toward the wafery part 1. This may help installing any wires and circuitry for the high voltage application beneath the wafery part 1.

On the other hand, the other terminus of the first electrode 6 and the second electrode 7 are in contact with the ambient air and will be applied with a voltage. The voltage application may be convenient in such a way that the first electrode 6 should be connected to a voltage potential HV while the second electrode 7 to the earth potential.

Since a voltage will be applied between the first electrode 6 and the second electrode 7, an electroosmotic flow will be developed there between to move the entire liquid sample 21 in the passages 2 toward the second electrode 7. At the same time the fluid will undergo with an electrophoresis separation, several kinds of materials which are contained in the liquid sample 21 will be separated into bands. More specifically, an electroosmotic flow makes move of the liquid sample 21 in the capillaries 2 at a certain rate of flow, and specimen materials (charged particles or ions and neutral molecules and the like) contained in the liquid sample 21 to be moved are separated each from other by their mobility difference. As a result fluid containing isolated sample matter resides at some points along the capillaries 2, making several bands of sample material isolated from within the solution. After some times the bands isolated each from other reach to the very end of the capillaries 2, ultimately in sequence.

Sample molecules separated into bands as have been described above may be detected in an optical method, by using an optical microscope or a confocal microscope to video-record. More specifically, the optical detection methods include a method of labeling the sample molecules isolated into bands with fluorescent marker to visualize the sample material (isolated sample molecules) by means of fluorescent detection by laser excitation. This method is such that the fluorescence light emitted from the sample molecules isolated into bands is detected by a photomultiplier tube or a CCD (charge coupled device) camera. When the observation region obtained as an image by the CCD camera is vast, a plurality of capillaries (passages) 2 are observed simultaneously to enable optical analysis of the liquid sample.

A packing 8 is interposed between the wafery part 1 and the device 3 of the capillary electrophoresis system for the purpose of watertight seal. When the packing 8 is broken the buffer solution may flow out to the bottom of the wafery part 1. In such a case the first electrode 6 and the second electrode 7 will be conducted through the effluent buffer to make a short circuit. This problem may be avoided by providing a liquid reservoir 3a on the device 3.

Now referring to FIG. 3, there is shown an overview of the first embodiment of capillary electrophoresis system shown in FIG. 1 viewed from the topsite. The wafery part 1 will be displaced in stepwise in the horizontal direction (direction of the drawing plane) by means of a stepping motor and the like. In the embodiment shown in FIG. 3, the wafery parts 1 are placed separated apart each from another at a regular interval. By moving one channel at a time by an event distance at every regular intervals, a voltage will be applied across the first electrode 6 and the second electrode 7 to form an electroosmotic flow in one capillary, so that the liquid sample 21 contained in one capillary (passages) 2 will be moved toward the second electrode 7, then at the same time to isolate by the electrophoresis several kinds of materials contained in the liquid sample 21 into bands. Those materials (sample molecules) isolated into bands may be analyzed in such a way as by optical analysis such as the fluorescence light detection or optical density (OD) measurement as have been described above, or by transforming into gaseous ions by the sonic splay ionization technique to be analyzed in a mass spectrometer installed in a vacuum chamber.

To achieve the analysis, in the structural aspect, the first buffer reservoir 4 and the second buffer reservoir 5 are tailored to be smaller than the interval between passages 2 so as to communicate at each moving distance of the wafery part 1 to at most one passage 2.

In the temporal aspect, in the electrophoresis, an analytical session may last in approximately 20 seconds. Therefore the wafery part 1 may move every 20 seconds. To protect against electrical leak, it is preferable to abort the voltage application to the first electrode 6 and the second electrode 7 during moving the wafery part 1.

Figure 4:
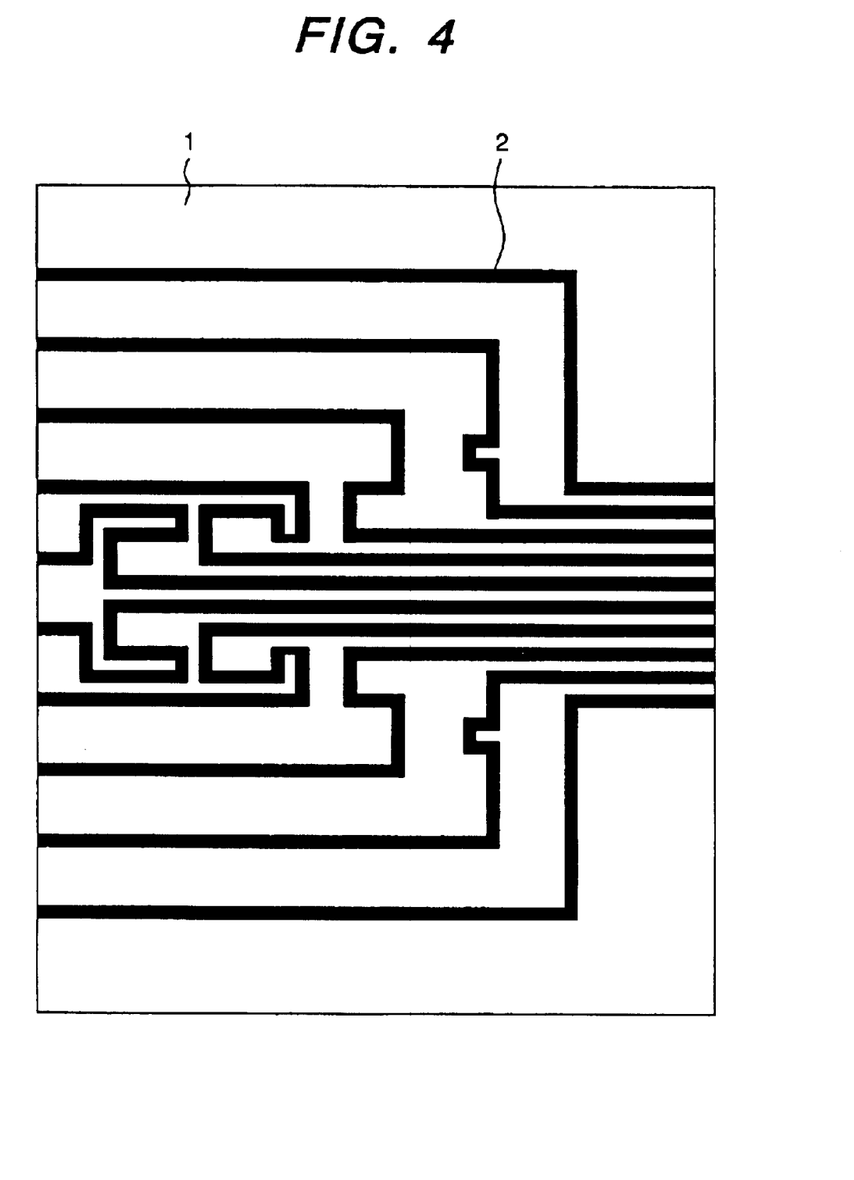
FIG. 4 is a top view showing a second embodiment of the wafery part in accordance with the present invention.

Now referring to FIG. 4, there is shown a schematic diagram illustrating the second embodiment of the wafery part 1 having passages 2 in accordance with the present invention. In the second preferred embodiment, the interval between passages 2 at the inlet of the liquid sample at the left side is larger than the interval of passages 2 at the right side. In other words the distance between passages 2 in the sample inlet at the left side is set to be 2 millimeters or more to facilitate the loading of liquid sample, while the distance between passages 2 of the detector side at the right hand is made smaller to facilitate the displacement of entire range by means of a precise position adjuster.

To assure the repeatability of electrophoresis, the shape of passages 2 will be tailored such that all passages 2 have the same length.

The volume of sample solution to be loaded into the passages 2 may be approximately 10 nanolitters, implicitly requiring a high sensitivity instrument for detecting the isolated matters, such as a mass spectrometer.

Figure 5:
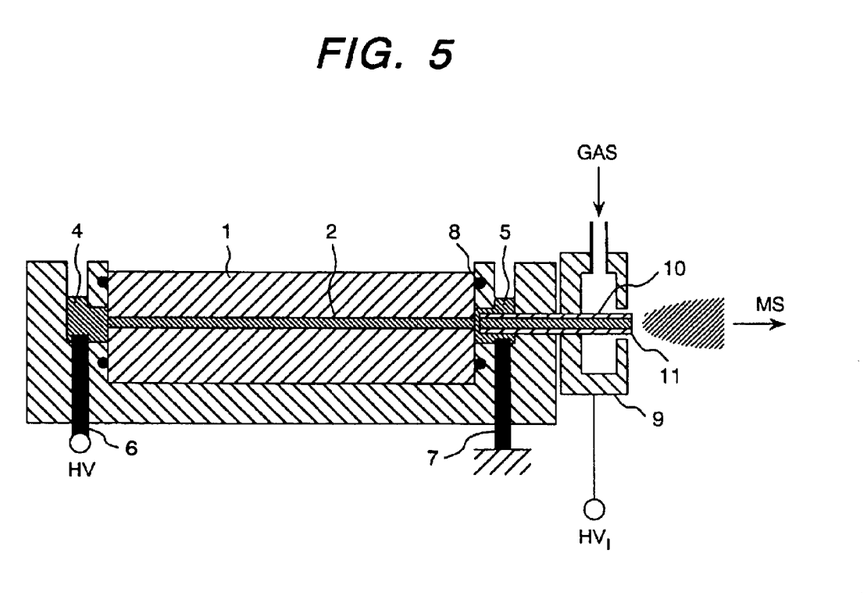
FIG. 5 is a schematic cross-sectional view in the vertical direction illustrating a capillary electrophoresis system connected to an ion source of a mass spectrometer in accordance with the present invention.

Now referring to FIG. 5, there is shown a schematic cross-sectional view in the vertical direction of a capillary electrophoresis system connected to an ion source of a mass spectrometer MS in accordance with the present invention. In this preferred embodiment, the matters in the liquid sample isolated by an electrophoresis assay, are transformed into gaseous ions by the sonic splay ionization technique to feed to the mass spectrometer MS installed in a vacuum chamber to analyze and determined the mass of ions. Ionization in the ion source 9 may be also effectuated by such methods as atmospheric pressure chemical ionization, electrospray ionization, and however these methods may restrict the composition of buffer solution. More specifically, in another ionization such as electrospray ionization method, ions cannot be generated in a stable manner from a solution having a high electric conductivity such as the PBS.

The analyzer for analyzing several kinds of material (sample molecules) to be isolated may be a spectrofluorometer, optical density spectrometer, and electrode spectrometry rather than the mass spectrometry MS.

In the system shown in FIG. 5, the mixture (a liquid sample containing several matters) can be isolated and analyzed rapidly. In the ion source 9 for transforming the liquid sample into gaseous ions, the liquid sample 21 containing several matters (sample molecules) isolated by the electrophoresis is sprayed with a sonic gas flow (the sonic splay ionization). The detailed discussion on the sonic splay ionization can be seen in the "Trends in Analytical Chemistry", Vol. 16, pp. 45–52 (1997).

As shown in FIG. 5, the structure of the ion source 9 is just like a nebulizer. The liquid sample isolated by the electrophoresis by the electroosmotic flow will be loaded into the silica capillary 10 having an inner diameter of approximately 50 micrometers. One end of capillary 10 is inserted into an orifice 11 of the ion source 9.

Nitrogen gas is introduced from the above into the ion source 9 to release the gas to the environment through the orifice 11 at the sonic speed. The sample solution loaded into the capillary 10 is ionized by the sonic gas flow. The gaseous ions generated in the ambient air are captured into the vacuum chamber to perform a mass analysis by means of a mass spectrometer MS not shown in the figure but installed in the vacuum chamber.

The solution loaded in the capillary 10 is sucked by the sonic gas flow. The flow rate of sucked flow may be higher than the flow rate of electrooemotic flow in the passages 2. Therefore, to avoid this, the ends of the passages 2 are placed at a very narrow distance to the capillary 10 of one millimeter or less so as not to directly connect to the capillary 10. In this arrangement the exact amount required of buffer solution in the second buffer reservoir 5 is sucked into the capillary 10 while preventing the liquid sample 21 in the passages 2 from being spilled out in order not to affect the electrophoresis via one end of the passages 2.

In the above configuration, the center axis of outlet passages 2 and the inlet capillary 10 need to be aligned as precise as possible. If there is a significant offset therebetween part of solution spilled from the passages 2 may not be directed into the capillary 10 to cause a problem of sensitivity of detection and a repeatability.

The voltage to be applied in the system shown in FIG. 5 will be such that the potential of the second electrode 7 is set to the ground potential while a high voltage HV of approximately 3 kilovolts for electrophoresis is applied to the first electrode 6. In addition if another voltage HVI of approximately 1.2 kilovolts is applied to the ion source 9, a large quantity of ions comprised of the materials in the sample solution charged to a potential opposite to the polarity of the voltage will be generated. The polarity of the voltage applied to the ion source 9 can be selectable depending on the ion potential of the materials to be detected.

The wafery part 1 may also be used for the purpose of sample introduction by introducing only the liquid sample 21 into the passages 2 (capillaries) of the wafery part 1. In this case, the buffer solution does not be introduced to the wafery part 1.

Figure 6:
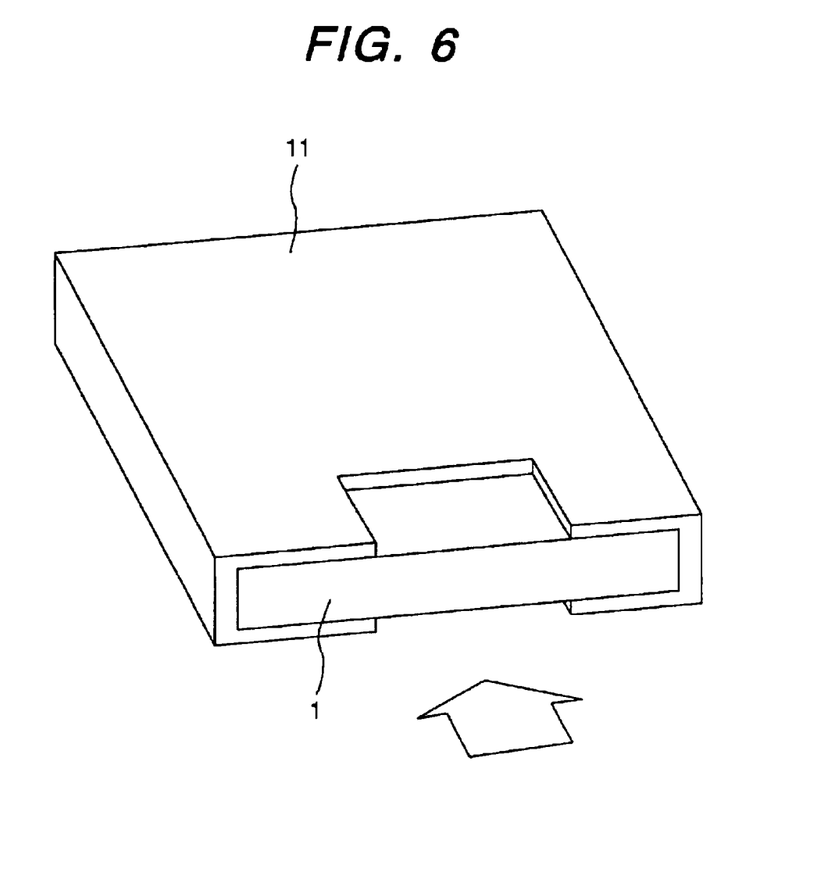
FIG. 6 is an electrophoresis sample cassette with a wafery part attached in a removable holder in accordance with the present invention.

Now referring to FIG. 6, there is shown a schematic diagram in which the wafery part 1 for capillary electrophoresis system in accordance with the present invention is removably attached to a sample holder 11. In a combination of capillary electrophoresis with a mass spectrometry (CE/MS) as shown in FIG. 5, the installation may become large. Therefore the liquid sample 21 may be conveniently prepared to introduce into the passages 2 (capillaries) of the wafery part 1 so as to carry wafery part 1 attached to a sample holder 11. More specifically, the watery part 1 having passages 2 (capillaries) having liquid sample 21 introduced for the capillary electrophoresis system in accordance with the present invention can be removably attached to a sample holder 11. The solution 21 and 22 in the very fine structure being loaded in the passages 2 (capillaries) of the watery part 1 to be removably attached to the sample holder 11 are unlikely to be intermixed so that there is not a problem of transportation for a while. By watertightly sealing the liquid sample 21 and 22 in the sample holder 11 the evaporation of samples 21 and 22 can be prevented.

The tolerable time to load the sample into the capillary electrophoresis system device 3 can be prolongated by freezing the wafery part 1 together with the sample solution 21 loaded in the sample holder 11.

The sample holder 11 may be preferable made of a fluoroplastic resin.

As can be appreciated from the foregoing description, as shown in FIG. 6, a sample cassette for electrophoresis separation that houses the sample holder 11 in which is removably attached (inserted) the wafery part 1 having passages 2 (capillaries) containing the liquid sample solution 21 allows carrying samples to the capillary electrophoresis system device 3.

Figure 7:
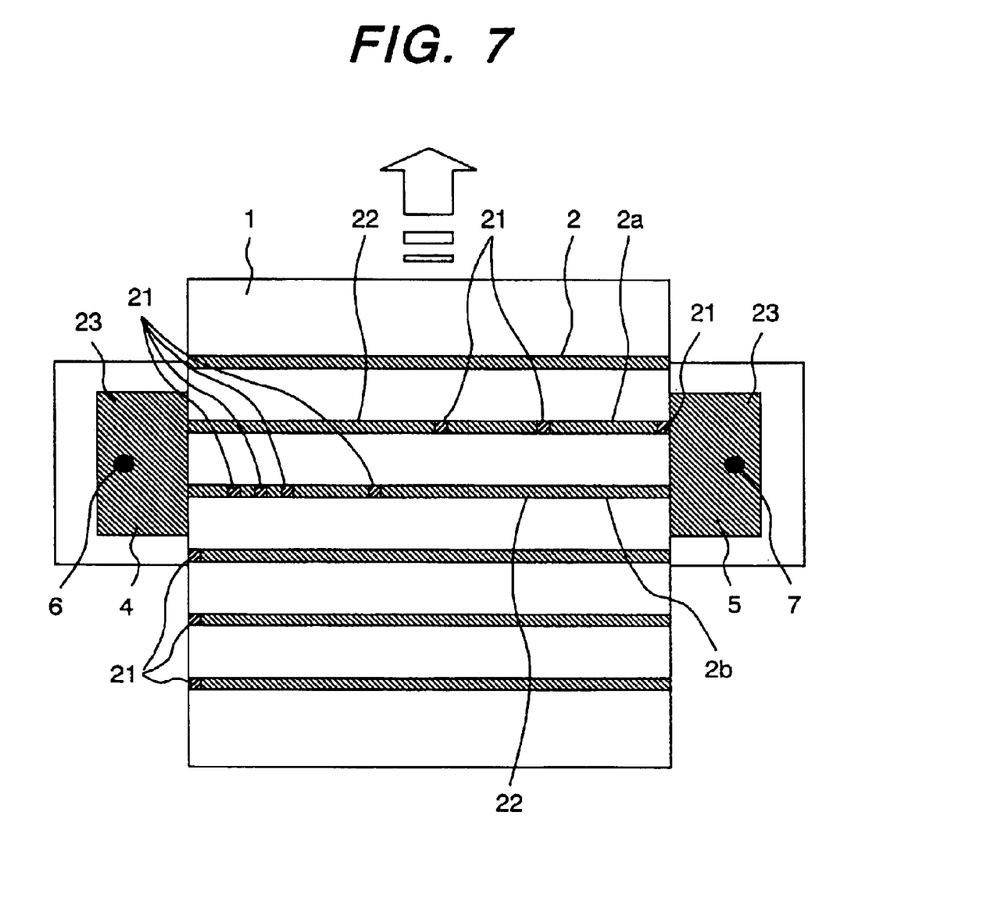
FIG. 7 is a top view of the second embodiment of capillary electrophoresis system in accordance with the present invention.

Now referring to FIG. 7, there is shown a plan view of a second embodiment of the capillary electrophoresis system suitable for the separation of one sample solution in accordance with the present invention. In the second preferred embodiment, the liquid sample 21 in a plurality of passages 2 can be electrophoresis separated because the first buffer reservoir 4 and the second buffer reservoir 5 are enlarged. More specifically, the solution 21 and 22 in a plurality of passages 2 (capillaries) are applied with a voltage, so that the liquid sample 21 in the passages 2 (capillaries) can be electrophoresis separated. The starting time of separation of respective liquid sample 21 in each of the passages 2 can be shifted in accordance with moving in either a continuous or a stepwise manner the wafery part 1 and shifting the timing of applying the voltage thereto to shift the starting time of electrophoresis. More specifically, as a passage (capillary) 2a is to be first applied with a voltage, the sample solution 21 in the passage (capillary) 2a can be first electrophoresis separated. Then followed by the capillary 2a, a voltage is applied to another passage (capillary) 2b, so that the liquid sample 21 in the capillary 2b can be second electrophoresis separated. In this manner, stepwise or continuous movement of the wafery part 1 may cause the starting time of electrophoresis to be delayed by shifting the applying timing of voltage to allow the starting time of electrophoresis for each of liquid samples 21 in the passages 2 to be shifted each other.

Figure 8:
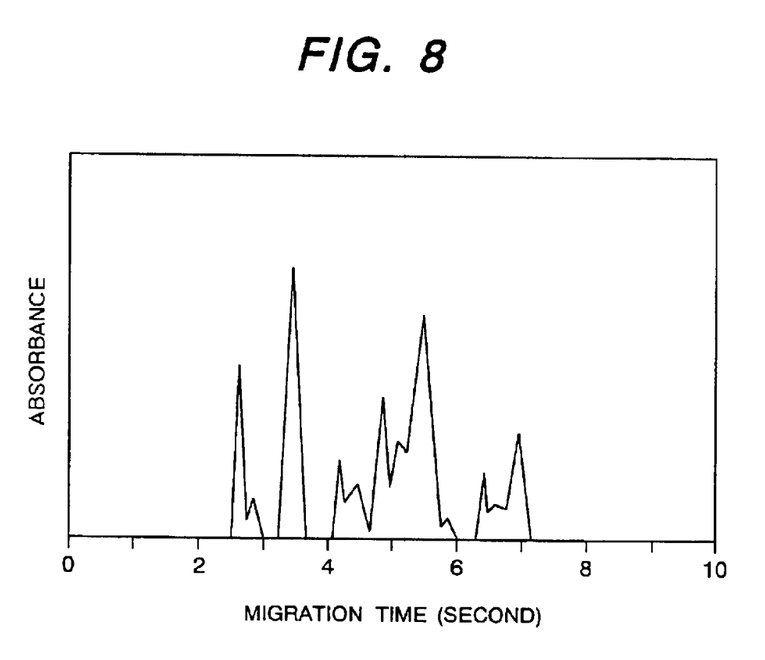
FIG. 8 is a graph showing an electrophoresis pattern.

Now referring to FIG. 8 there is an exemplary graph illustrating an electrophoresis result obtained by the separation of one single liquid sample 21 as shown in FIG. 7. The ordinate (y-axis) indicates the absorbance of the solution separated, and the abscissa indicates the migration time. Peaks in FIG. 8 denote to the presence of matters. Before approximately 2 seconds from the start of electrophoresis, there is not appeared a peak. This indicates that the 2 seconds at the start of electrophoresis has no significance in observation. Furthermore, when analyzing the concentration of a specific matter, it is sufficient to detect the peak of that matter only when that peak appears in the electrophoresis pattern. Any other observation may be useless. Therefore, it is convenient to shift the starting time of electrophoresis separation of the liquid sample 21 as shown in FIG. 5 if a number of samples 21 need to be analyzed in a period of time as short as possible. In addition, if it is sufficient to detect only one specific matter, the analysis can be completed at the speed of one sample per second since the time required for analyzing one liquid sample is approximately 1 second.

In accordance with the capillary electrophoresis system of the present invention, a plurality of samples may be completed to be analyzed in a shorter time.

Since the liquid sample 21 is introduced into a cartridge-type wafery part 1, the wafery part 1 can be carried with the sample loaded therein. The wafery part 1 may be rinsed easily and can be iteratively reused.

The foregoing description of the preferred embodiments of the invention has been presented for purposes of illustration and description thereof. It is not intended to be exhaustive or to limit the invention to the precise form disclosed, and modifications and variations are possible in light of the above teachings or may be acquired from practice of the invention. The embodiments chosen and described herein in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A capillary electrophoresis system, comprising:
    a wafer-shaped part having passages for introducing sample solutions;
    a body having a configuration suitable to removably hold and to move said wafer-shaped part relatively to said wafer shaped part; and
    means for moving the wafer-shaped part relative to said body to form an electroosmotic flow sequentially in said passages;
    wherein said body includes,
    first and second electrodes for applying a voltage between both ends of passages of said wafer-shaped part for electrophoresis, and
    first and second buffer reservoirs conductive to said passages for filling buffer solution around said first and second electrodes.

2. A capillary electrophoresis system according to claim 1, wherein said wafer-shaped part is made of a dielectric material.

3. A capillary electrophoresis system according to claim 1, wherein said passages are formed in said wafer-shaped part at an even interval at least in an end of passages.

4. A capillary electrophoresis system according to claim 1, wherein at least part of said wafer-shaped part is formed of a dielectric material.

5. A capillary electrophoresis system, comprising:
    a wafer-shaped part having said passages filled with a buffer solution for introducing sample solutions together;
    a body having a configuration suitable to removably hold and to move said wafer-shaped part attached in a relative manner; and
    means for moving the wafer-shaped part relative to said body to form an electroosmotic flow sequentially in said passages;
    wherein said body includes:
    first and second electrodes for applying a voltage between both ends of passages of said wafer-shaped part to separate and take out said sample solutions; and
    first and second buffer reservoirs conductive to said passages of said wafer-shaped part at a specific position for filling buffer solution around said first and second electrodes.

6. A capillary electrophoresis system according to claim 5, wherein said wafer-shaped part is made of a dielectric material.

7. A capillary electrophoresis system according to claim 5, wherein said passages are formed in said wafer-shaped part at an even interval at least in an end of passages.

8. A sample analyzing system comprising:
    a capillary electrophoresis system having a wafer-shaped part having passages for introducing a sample solution, a body having a configuration suitable to removably hold and to move said wafer-shaped part attached in a relative manner and means for moving the wafer-shaped part relative to said body to form an electroosmotic flow sequentially in said passages, in which said body includes first and second electrodes for applying a voltage across both ends of passages of said wafer-shaped part to separate and take out said sample solution, and first and second buffer reservoirs conductive to said passages of said wafer-shaped part at a specific position for filling buffer solution around said first and second electrodes; and
    an analyzer for optically detecting and analyzing a sample that is electrophoretically separated by said capillary electrophoresis system.

9. A sample analyzing system comprising:
    a capillary electrophoresis system having a wafer-shaped part having passages filled with buffer solution for introducing a sample solution, a body having a configuration suitable to removably hold and to move said wafer-shaped part attached in a relative manner and means for moving the wafer-shaped part relative to said body to form an electroosmotic flow sequentially in said passages, in which said body includes first and second electrodes for applying a voltage across both ends of passages of said wafer-shaped part to separate and take out said sample solution, and first and second buffer reservoirs conductive to said passages of said wafer-shaped part at a specific position for filling buffer solution around said first and second electrodes; and an analyzer for optically detecting and analyzing the solution having electrophoresis separated by said capillary electrophoresis system.

10. A sample analyzing system comprising:

a capillary electrophoresis system having a wafer-shaped part having passages for introducing a sample solution, a body having a configuration suitable to removably hold and to move said wafer-shaped part attached in a relative manner and means for moving the wafer-shaped part relative to said body to form an electroosmotic flow sequentially in said passages, in which said body includes first and second electrodes for applying a voltage across both ends of passages of said wafer-shaped part to separate and take out said sample solution, and first and second buffer reservoirs conductive to said passages of said wafer-shaped part at a specific position for filling buffer solution around said first and second electrodes;

an ion source connected to one of said buffer reservoirs of said capillary electrophoresis system for ionizing the solution spilled from said wafer-shaped part into gaseous ions; and a mass spectrometer for performing mass analysis of the ions emitted from said ion source.

11. A sample analyzing system comprising:

a capillary electrophoresis system having a wafer-shaped part having passages for introducing a sample solution, a body having a configuration suitable to removably hold and to move said wafer-shaped part attached in a relative manner and means for moving the wafer-shaped part relative to said body to form an electroosmotic flow sequentially in said passages, in which said body includes first and second electrodes for applying a voltage across both ends of passages of said wafer-shaped part to separate and take out said sample solution, and first and second buffer reservoirs conductive to said passages of said wafer-shaped part at a specific position for filling buffer solution around said first and second electrodes;

an ion source connected to one of said buffer reservoirs of said capillary electrophoresis system for ionizing the sample solution isolated by electrophoresis from said wafer-shaped part into gaseous ions; and a mass spectrometer for performing mass analysis of the ions emitted from said ion source.

12. A sample analyzing system comprising:

a capillary electrophoresis system having a wafer-shaped part having passages filled with buffer solution for introducing a sample solution, a body having a configuration suitable to removably hold and to move said wafer-shaped part attached in a relative manner and means for moving the wafer-shaped part relative to said body to form an electroosmotic flow sequentially in said passages, in which said body includes first and second electrodes for applying a voltage across both ends of passages of said wafer-shaped part to separate and take out said sample solution, and first and second buffer reservoirs conductive to said passages of said wafer-shaped part at a specific position for filling buffer solution around said first and second electrodes;

an ion source connected to one of said buffer reservoirs of said capillary electrophoresis system for ionizing the solution spilled from said wafer-shaped part into gaseous ions; and a mass spectrometer for performing mass analysis of the ions emitted from said ion source.

* * * * *